United States Patent
Meng et al.

(10) Patent No.: US 9,338,819 B2
(45) Date of Patent: May 10, 2016

(54) VARIABLE DATA USAGE PERSONAL MEDICAL SYSTEM AND METHOD

(71) Applicant: Medtronic MiniMed, Inc., Northridge, CA (US)

(72) Inventors: Fan Meng, Pasadena, CA (US); Gary A. Cohen, Sherman Oaks, CA (US); Eileen H. Dempster, West Hills, CA (US); George W. Patterson, Rancho Palos Verdes, CA (US); Cary D. Talbot, Santa Clarita, CA (US); Mark Sebastian Verghese, Santa Monica, CA (US); Maral Gharib, Altadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 244 days.

(21) Appl. No.: 13/904,343

(22) Filed: May 29, 2013

(65) Prior Publication Data
US 2014/0357972 A1     Dec. 4, 2014

(51) Int. Cl.
| | |
|---|---|
| H04W 88/00 | (2009.01) |
| A61M 5/142 | (2006.01) |
| H04W 4/00 | (2009.01) |
| G06F 19/00 | (2011.01) |
| A61B 5/145 | (2006.01) |
| A61M 5/172 | (2006.01) |

(52) U.S. Cl.
CPC .......... *H04W 88/00* (2013.01); *A61M 5/14244* (2013.01); *G06F 19/3418* (2013.01); *H04W 4/00* (2013.01); *A61B 5/14532* (2013.01); *A61M 5/1723* (2013.01); *A61M 2005/14208* (2013.01); *A61M 2202/07* (2013.01); *A61M 2205/18* (2013.01); *A61M 2205/3553* (2013.01); *A61M 2205/3561* (2013.01); *A61M 2205/3576* (2013.01); *A61M 2205/3584* (2013.01); *A61M 2205/3592* (2013.01); *A61M 2230/005* (2013.01); *A61M 2230/201* (2013.01); *H04W 4/008* (2013.01)

(58) Field of Classification Search
CPC ........................... H04W 88/00; A61M 5/14244
USPC .......................................................... 709/217
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

OTHER PUBLICATIONS

Raghavan et al., "Cloud Control with Distributed Rate Limiting", 2007.*
Wu et al., "MPEG-4 Compressed Video Over the Internet", 1999.*

*Primary Examiner* — O. C. Vostal
(74) *Attorney, Agent, or Firm* — Medtronic Minimed, Inc.

(57) ABSTRACT

A variable data usage personal medical system including a self-care device attached to a patient, and operable to generate self-care device data and to transmit the self-care device data at a fixed interval; a cellular communication device operable to receive and store the transmitted self-care device data, to register a count at an interval counter for each of the fixed intervals in which the transmitted self-care device data is received, to generate a data cellular packet from overhead plus the stored self-care device data when the interval counter equals a fixed interval index, and to transmit the data packet; and a cloud infrastructure operably connected to the cellular communication device over a cellular network, and operable to receive, process, and store the transmitted data packet. The cloud infrastructure is operable to transmit a value for the fixed interval index to the cellular communication device for storage.

18 Claims, 13 Drawing Sheets

(56) References Cited

U.S. PATENT DOCUMENTS

| | | | |
|---|---|---|---|
| 5,485,408 A | 1/1996 | Blomquist | |
| 5,522,803 A | 6/1996 | Teissen-Simony | |
| 5,560,021 A * | 9/1996 | Vook | H04W 52/286 709/227 |
| 5,665,065 A | 9/1997 | Colman et al. | |
| 5,760,705 A * | 6/1998 | Glessner | H04W 84/025 340/4.21 |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,091,362 A * | 7/2000 | Stilp | G01S 5/02 342/457 |
| 6,186,982 B1 | 2/2001 | Gross et al. | |
| 6,201,976 B1 * | 3/2001 | Rasanen | H04W 76/02 370/209 |
| 6,244,758 B1 * | 6/2001 | Solymar et al. | 709/224 |
| 6,246,992 B1 | 6/2001 | Brown | |
| 6,248,067 B1 | 6/2001 | Causey, III et al. | |
| 6,248,093 B1 | 6/2001 | Moberg | |
| 6,287,252 B1 * | 9/2001 | Lugo | 600/300 |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,078,759 B2 * | 12/2011 | Seifert | G06F 17/30899 709/232 |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,386,560 B2 * | 2/2013 | Ma | G06T 15/005 709/203 |
| 8,963,692 B2 * | 2/2015 | Sanders | 340/10.42 |
| 2002/0031086 A1 * | 3/2002 | Welin | 370/229 |
| 2003/0069025 A1 * | 4/2003 | Hoctor et al. | 455/456 |
| 2003/0172179 A1 * | 9/2003 | del Prado Pavon | H04J 3/0655 709/236 |
| 2003/0208614 A1 * | 11/2003 | Wilkes | G06F 3/0601 709/232 |
| 2005/0003824 A1 * | 1/2005 | Siris | H04L 47/10 455/452.1 |
| 2005/0111407 A1 * | 5/2005 | Hosein | H04W 28/22 370/329 |
| 2005/0277872 A1 * | 12/2005 | Colby et al. | 604/67 |
| 2006/0122864 A1 * | 6/2006 | Gottesman et al. | 705/2 |
| 2007/0002791 A1 * | 1/2007 | Kasprzyk et al. | 370/328 |
| 2007/0078320 A1 * | 4/2007 | Stafford | 600/347 |
| 2007/0110053 A1 * | 5/2007 | Soni | H04L 63/0263 370/389 |
| 2007/0123819 A1 | 5/2007 | Mernoe et al. | |
| 2007/0233888 A1 * | 10/2007 | Yamaki | G06F 19/3406 709/230 |
| 2008/0004904 A1 * | 1/2008 | Tran | A61B 5/0006 705/2 |
| 2008/0024307 A1 * | 1/2008 | Wissendheit | H01Q 1/22 340/572.7 |
| 2008/0088438 A1 * | 4/2008 | Aninye et al. | 340/539.13 |
| 2008/0263150 A1 * | 10/2008 | Childers | H04L 41/0853 709/203 |
| 2009/0161587 A1 * | 6/2009 | Ishii et al. | 370/311 |
| 2010/0160861 A1 | 6/2010 | Causey, III et al. | |
| 2010/0185794 A1 * | 7/2010 | Belyakov | H04L 69/40 710/38 |
| 2010/0228878 A1 * | 9/2010 | Xu | G06F 9/544 709/233 |
| 2011/0093285 A1 * | 4/2011 | Dicks et al. | 705/2 |
| 2011/0183698 A1 * | 7/2011 | Hoctor et al. | 455/509 |
| 2012/0130737 A1 * | 5/2012 | Finizio et al. | 705/2 |
| 2012/0131195 A1 * | 5/2012 | Morgan | G06F 9/5072 709/226 |
| 2012/0242501 A1 * | 9/2012 | Tran | A61B 5/0024 340/870.02 |
| 2012/0269163 A1 * | 10/2012 | Edara | H04W 24/00 370/331 |
| 2013/0007210 A1 * | 1/2013 | Mass et al. | 709/217 |
| 2013/0031224 A1 * | 1/2013 | Nachtrab | G06F 21/6218 709/220 |
| 2013/0127980 A1 * | 5/2013 | Haddick et al. | 348/14.08 |
| 2013/0191511 A1 * | 7/2013 | Liu | H04L 67/2847 709/219 |
| 2013/0204965 A1 * | 8/2013 | Masputra | H04L 47/60 709/217 |
| 2013/0231947 A1 * | 9/2013 | Shusterman | 705/2 |
| 2013/0329615 A1 * | 12/2013 | Vyas | H04W 52/0229 370/311 |
| 2014/0163402 A1 * | 6/2014 | Lamego et al. | 600/493 |
| 2014/0201354 A1 * | 7/2014 | Matthews | H04L 43/04 709/224 |
| 2014/0269369 A1 * | 9/2014 | Ghosh | H04W 74/08 370/252 |
| 2014/0273821 A1 * | 9/2014 | Miller | H04B 5/0043 455/41.1 |
| 2014/0282668 A1 * | 9/2014 | Gava | H04N 21/44213 725/19 |

* cited by examiner

| 510 | 520 | 530 | 540 |
|---|---|---|---|
| Alarm Number | Alarm Name | Notification Text Message | Accompanying Data |
| *Sensor Alert* | | | |
| A101 | "High SG" - Measured glucose is above user specified high limit | HIGH SG nnn/nn.n <mg/dL>/<mmol/L | SG: time stamp, value, trend arrow<br>Last Bolus: time, type (normal, square, dual), amount<br>Active Insulin: amount<br>Basal: current basal rate<br>Temp basal: insulin rate, duration<br>Suspend: when, how long<br>BG: time stamp, value<br>Meal: time of the meal, type (protein, Sat. fat, fiber, Cholesterol, Carbohydrates), amount, unit (grams, exchange), calories<br>Exercise: time, duration, intensity<br>Stress: cause (illness, physical, emotional - life changes, work, relationship, financial; menstrual)<br>Illness: pain, heart disease, sleep problem<br>Medication: time, type, dose |
| A102 | "Low SG" - Measured glucose is above user specified low limit | LOW SG nnn/nn.n <mg/dL>/<mmol/L | SG: time stamp, value, trend arrow<br>Last Bolus: time, type (normal, square, dual), amount<br>Active Insulin: amount<br>Basal: current basal rate<br>Temp basal: insulin rate, duration<br>BG: time stamp, value<br>Last Meal: time of the meal, type (protein, Sat. fat, fiber, Cholesterol, Carbohydrates), amount, unit (grams, exchange), calories<br>Exercise: time, duration, intensity<br>Stress: cause (illness, physical, emotional - life changes, work, relationship, financial; menstrual)<br>Illness: infection, cancer, liver and kidney disease<br>Medication: time, type, dose |
| A 103 | "Low Suspend" - Measured glucose is at or below user specified low suspend limit | LOW SUSPEND Glucose is below Low Suspend limit. Delivery stopped | SG: time stamp, value, trend arrow<br>Last Bolus: time, type (normal, square, dual), amount<br>Active insulin: amount<br>Basal: current basal rate<br>Temp basal: insulin rate, duration |

↓ A/B                 FIG. 5A                 A/B ↓

| | | | |
|---|---|---|---|
| | "Low Suspend" - Measured glucose or Predictive Low SGV is at or below user specified low suspend limit | | BG: time stamp, value<br>Last Meal: time of the meal, type (protein, Sat. fat, fiber, Cholesterol, Carbohydrates), amount, unit (grams, exchange), calories<br>Exercise: time, duration, intensity<br>Stress: cause (illness, physical, emotional - life changes, work, relationship, financial; menstrual)<br>Illness: infection, cancer, liver and kidney disease<br>Medication: time, type, dose |
| A 104 | "Meter BG Now" - Meter BG calibration required now | METER BG NOW<br>Sensor values not available;<br>enter a new BG now | Current SG: time stamp, value, trend arrow<br>Last BG: time stamp, value |
| A 105 | "Meter BG by hh:mm" - Meter BG calibration required by a user specified time | METER BG BY<br>This is a reminder to enter meter BG soon | Current SG: time stamp, value, trend arrow<br>Last BG: time stamp, value |
| A 106 | "Cal Error" - The range between the meter BG reading and sensor BG readings is too far apart | CAL ERROR<br>Invalid sensor data or invalid BG value | Current SG: time stamp, value, trend arrow<br>Last BG: time stamp, value |
| A 107 | "Sensor End" - Sensor is at end of life | SENSOR END<br>Replace sensor<br>See user guide | Current SG: time stamp, value, trend arrow<br>Last BG: time stamp, value<br>SG: last 3 hours of SG data to plot trend |
| A 108 | "Change Sensor" - Bad or noisy sensor readings, sensor has failed. Sensor must be replaced | CHANGE SENSOR<br>See user guide | Current SG: time stamp, value, trend arrow<br>Last BG: time stamp, value<br>SG: last 3 hours of SG data to plot trend |
| A 109 | "Sensor Error" - Sensor self-test failed | SENSOR ERROR<br>Invalid sensor value<br>See user guide | |
| A 110 | "Charge Transmtr" - Dead sensor battery | CHARGE TRANSMITTER | |
| A 111 | "Low Transmtr" - Low sensor battery | LOW TRANSMITTER<br>Charge transmitter now | |

FIG. 5B

| | | | |
|---|---|---|---|
| A 112 | "Weak Signal" - Pump/monitor did not receive up to 8 transmitter packets | WEAK SIGNAL Move pump closer to sensor See user guide | |
| A 113 | "Lost Sensor" - Pump/monitor lost sync with transmitter | LOST SENSOR Sensor values not available; go to Find Lost Sensor See user guide | |
| A 114 | "High Predicted" - Predicted Glucose value is at or above the High Glucose Warning Limit | HIGH PREDICTED Glucose may be higher or equal to user specified limit at specified time | SG: time stamp, value, trend arrow Last Bolus: time, type (normal, square, dual), amount Active insulin: amount Basal: current basal rate Temp basal: insulin rate, duration Suspend: when, how long BG: time stamp, value Meal: time of the meal, type (protein, Sat. fat, fiber, Cholesterol, Carbohydrates), amount, unit (grams, exchange), calories Exercise: time, duration, intensity Stress: cause (illness, physical, emotional - life changes, work, relationship, financial; menstrual) Illness: pain, heart disease, sleep problem Medication: time, type, dose |
| A 115 | "Low Predicted" - Predicted Glucose value is at or below the Low Glucose Warning Limit | LOW PREDICTED Glucose may be lower or equal to user specified limit at specified time | SG: time stamp, value, trend arrow Last Bolus: time, type (normal, square, dual), amount Active insulin: amount Basal: current basal rate Temp basal: insulin rate, duration BG: time stamp, value Last Meal: time of the meal, type (protein, Sat. fat, fiber, Cholesterol, Carbohydrates), amount, unit (grams, exchange), calories Exercise: time, duration, intensity Stress: cause (illness, physical, emotional - life changes, work, relationship, financial; menstrual) Illness: infection, cancer, liver and kidney disease Medication: time, type, dose |

| Alarm Number | Alarm Name | CareLink Notification Text Message | Accompanying Data |
|---|---|---|---|
| A 116 | "Rise Rate" - Rising Rate of Change is equal or higher than the specified limit | RISE RATE Glucose rising rate of change is equal or higher than specified rate | SG: time stamp, value, trend arrow<br>Last Bolus: time, type (normal, square, dual), amount<br>Active insulin: amount<br>Basal: current basal rate<br>Temp basal: insulin rate, duration<br>Suspend: when, how long<br>BG: time stamp, value<br>Meal: time of the meal, type (protein, Sat. fat, fiber, Cholesterol, Carbohydrates), amount, unit (grams, exchange), calories<br>Exercise: time, duration, intensity<br>Stress: cause (illness, physical, emotional - life changes, work, relationship, financial; menstrual)<br>Illness: pain, heart disease, sleep problem<br>Medication: time, type, dose |
| A 117 | "Fall Rate" - Falling Rate of Change is equal or higher than the specified limit | FALL RATE Glucose falling rate of change is equal or higher than specified rate | SG: time stamp, value, trend arrow<br>Last Bolus: time, type (normal, square, dual), amount<br>Active insulin: amount<br>Basal: current basal rate<br>Temp basal: insulin rate, duration<br>BG: time stamp, value<br>Last Meal: time of the meal, type (protein, Sat. fat, fiber, Cholesterol, Carbohydrates), amount, unit (grams, exchange), calories<br>Exercise: time, duration, intensity<br>Stress: cause (illness, physical, emotional - life changes, work, relationship, financial; menstrual)<br>Illness: infection, cancer, liver and kidney disease<br>Medication: time, type, dose |
| A 88 | "Alert Silence" - An alert which is in Alert Silence mode has occurred | ALERT SILENCE One or more alerts have occurred during silence mode. Please check Sensor Alert History for details | |

*Pump Alert*

| Alarm Number | Alarm Name | CareLink Notification Text Message | Accompanying Data |
|---|---|---|---|
| A 81 | "Low Battery" - Low battery state | LOW BATTERY Replace battery now Use 1 AAA | |

| A 82 | "Low Reservoir" - Low reservoir limit setting has been reached, or the condition persists at 1hour remaining (or at 1/2 volume limit), causing the periodic indication to again be enabled | LOW RESERVOIR yy:yy hours remaining xxx.x units remaining | yy:yy hours remaining xxx.x units remaining |
|---|---|---|---|
| A 83 | "Check BG" - BG reminder duration elapsed | CHECK BG This is a reminder to check your BG | |
| A 84 | "Alarm Clock" - Alarm clock setting reached | ALARM CLOCK | |
| A 85 | "Max Fill Reached" - Requests user to confirm priming continuation | MAX FILL Check if tubing is full. See user guide | |
| A 87 | "Missed Bolus" - Missed Bolus reminder setting is reached | MISSED BOLUS? Reminder to eat or bolus | SG: time stamp, value, trend arrow Active insulin: amount Basal: current basal rate Temp basal: insulin rate, duration BG: time stamp, value Last Meal: time of the meal, type (protein, Sat. fat, fiber, Cholesterol, Carbohydrates), amount, unit (grams, exchange), calories |

*Pump Alarm*

| Alarm Number | Alarm Name | CareLink Notification Text Message | Accompanying Data |
|---|---|---|---|
| A03 | BATT OUT LIMIT" Battery removed for more than 10 minutes +0/-1 minute or until backup capacitor depletes | BATTERY OUT LIMIT Battery change too slow | |

| | | | |
|---|---|---|---|
| A04 | "No delivery" - Excess pressure from an improperly inserted reservoir or a clogged infusion set, not during a pump stroke | NO DELIVERY Delivery stopped Check BG See user guide to troubleshoot | Last SG: time stamp, value, trend arrow Active insulin: amount Basal: current basal rate Temp basal: insulin rate, duration BG: time stamp, value SG: last 3 hours of SG data to plot trend |
| | "No delivery" - The weighted average of the 5 force sensor readings exceeds the occlusion threshold during pump stroke | | |
| A05 | "OFF No Power" - Battery power depleted | NO POWER 0% battery life Delivery stopped Replace battery now | |
| A06 | "Auto Off" -No keys pressed in time duration set for Auto Off | AUTO OFF Delivery stopped No buttons pushed during time limit | |
| E 16 | "RESET" Settings cleared and pump reset by RF Diagnostics "Error Recovery Reset Pump" command | RESET Settings cleared by user Reprogram settings | Previous setting from pump: Max bolus Scroll Rate BG Reminder Basal profile Max basal Bolus wizard setting Easy bolus Sensor settings: on/off Glucose limit High/Low Predictive Alert |
| A 43 | "Motor Error" - A retry to free a stuck motor failed. If any motor stalls twice in a row a Stuck Motor fault condition is declared | MOTOR ERROR Delivery stopped Disconnect set | |

|  |  |  |  |
|---|---|---|---|
|  | "Motor Error" - Excessive motor drive counter during a pump stroke detected |  |  |
|  | "Motor Error" - Out of range average encoder velocity after rewind (Rewind Velocity Check) results in a Motor Error A |  |  |
|  | "Motor Error" - Failure of Drive Time Check after pump stroke movements generates a Motor Error alarm |  |  |
|  | "Motor Error" - Encoder Phase Error Check detected following a pump stroke |  |  |
|  | "Motor Error" - Attempt to deliver insulin following Encoder Error alarm (fault 70) results in issuance of a Motor Error alarm without any delivery of insulin |  |  |
| A 50 | "Bolus Stopped" - A battery out event occurred while a bolus or fixed prime was in progress | BOLUS STOPPED Loose battery cap? Pump dropped or bumped? Check bolus history, Reprogram bolus if required | Bolus history: last 4 hours Last SG: time stamp, value, trend arrow Active insulin: amount BG: time stamp, value |
| A 51 | "Max Delivery" - The maximum number of pump strokes allowed in an hour was exceeded ( | MAX DELIVERY Exceeded 1 hour max delivery Check BG | Last SG: time stamp, value, trend arrow Active insulin: amount BG: time stamp, value |

| ↑ H/I | | | H/I ↑ |
|---|---|---|---|
| A 66 | "No Reservoir"- A manual prime performed and the pump went all the way to the end of the possible encoder counts without detecting seating | NO RESERVOIR Delivery stopped Change reservoir | |
| A 74 | "Finish Loading" - User is not finished loading new reservoir process | FINISH LOADING Fill Cannula is not complete | |
| A 86 | "Weak Battery" - Battery voltage measurement on insertion detected a weak battery (<= 1.32V and > 1.28V) | WEAK BATTERY Shorter battery life expected | |
| Axx | | | |
| Exx | | | |

FIG. 51

VARIABLE DATA USAGE PERSONAL MEDICAL SYSTEM AND METHOD

TECHNICAL FIELD

The technical field of this disclosure is personal medical systems, particularly, variable data usage personal medical systems and methods.

BACKGROUND OF THE INVENTION

Advances in electronics and telemetry have resulted in the miniaturization of medical devices such that medical devices which previously required large stationary equipment can now be worn about the person, who can be monitored or receive treatment while pursuing normal daily tasks.

One area of such advances has been in the treatment of diabetes. An estimated twenty-six million people in the United States, or about 8% of the population, have diabetes. This percentage is expected to increase in the near-term as the population ages. Wearable glucose monitors and insulin pumps have been developed which allow persons under treatment for diabetes to be monitored and receive insulin while carrying on their day-to-day tasks.

Wearable medical devices oftentimes communicate with a remote computer system over a cellular network. Data, such as a glucose reading or pump information, is obtained at the person under treatment then sent to the computer system periodically for analysis. Unfortunately, data is often transmitted at a regular frequency which may be higher than what is required. Sending a large amount of data over a cellular network is expensive. Also, sending data too often can deplete the batteries on the personal medical device.

Other problems arise with the treatment of data received at the remote computer system. The data may not be current, making it unreliable and causing potential misdiagnosis of ongoing status. Further, alarms received at the remote computer system may be minimal, providing insufficient information on which to take appropriate corrective action.

It would be desirable to have a variable data usage personal medical system that would overcome the above disadvantages.

SUMMARY OF THE INVENTION

One aspect of the invention provides a variable data usage personal medical system for use with a patient including a self-care device attached to the patient, the self-care device being operable to generate self-care device data and to transmit the self-care device data at a fixed interval; a cellular communication device operably connected to the self-care device, the cellular communication device being operable to receive and store the transmitted self-care device data, to register a count at an interval counter for each of the fixed intervals in which the transmitted self-care device data is received, to generate a data cellular packet from overhead plus the stored self-care device data when the interval counter equals a fixed interval index, and to transmit the data packet; and a cloud infrastructure operably connected to the cellular communication device over a cellular network, the cloud infrastructure being operable to receive, process, and store the transmitted data packet. The cellular communication device is operable to store the fixed interval index and the cloud infrastructure is operable to transmit a value for the fixed interval index to the cellular communication device for storage.

Another aspect of the invention provides a method of personal medical variable data usage for a patient including transmitting a value for a fixed interval index remote from the patient; storing the fixed interval index at the patient; generating self-care device data for the patient; transmitting the self-care device data at a fixed interval; receiving and storing the transmitted self-care device data; registering a count at an interval counter for each of the fixed intervals in which the transmitted self-care device data is received; generating a data cellular packet from overhead plus the stored self-care device data when the interval counter equals the fixed interval index; transmitting the data packet from the patient over a cellular network; and receiving, processing, and storing the transmitted data packet remote from the patient.

Another aspect of the invention provides a system of personal medical variable data usage for a patient including means for transmitting a value for a fixed interval index remote from the patient; means for storing the fixed interval index at the patient; means for generating self-care device data for the patient; means for transmitting the self-care device data at a fixed interval; means for receiving and storing the transmitted self-care device data; means for registering a count at an interval counter for each of the fixed intervals in which the transmitted self-care device data is received; means for generating a data cellular packet from overhead plus the stored self-care device data when the interval counter equals the fixed interval index; means for transmitting the data packet from the patient over a cellular network; and means for receiving, processing, and storing the transmitted data packet remote from the patient.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 5A-5I is a table of alarms and accompanying data for a variable data usage personal medical system made in accordance with the invention.

DETAILED DESCRIPTION

Figure 1:
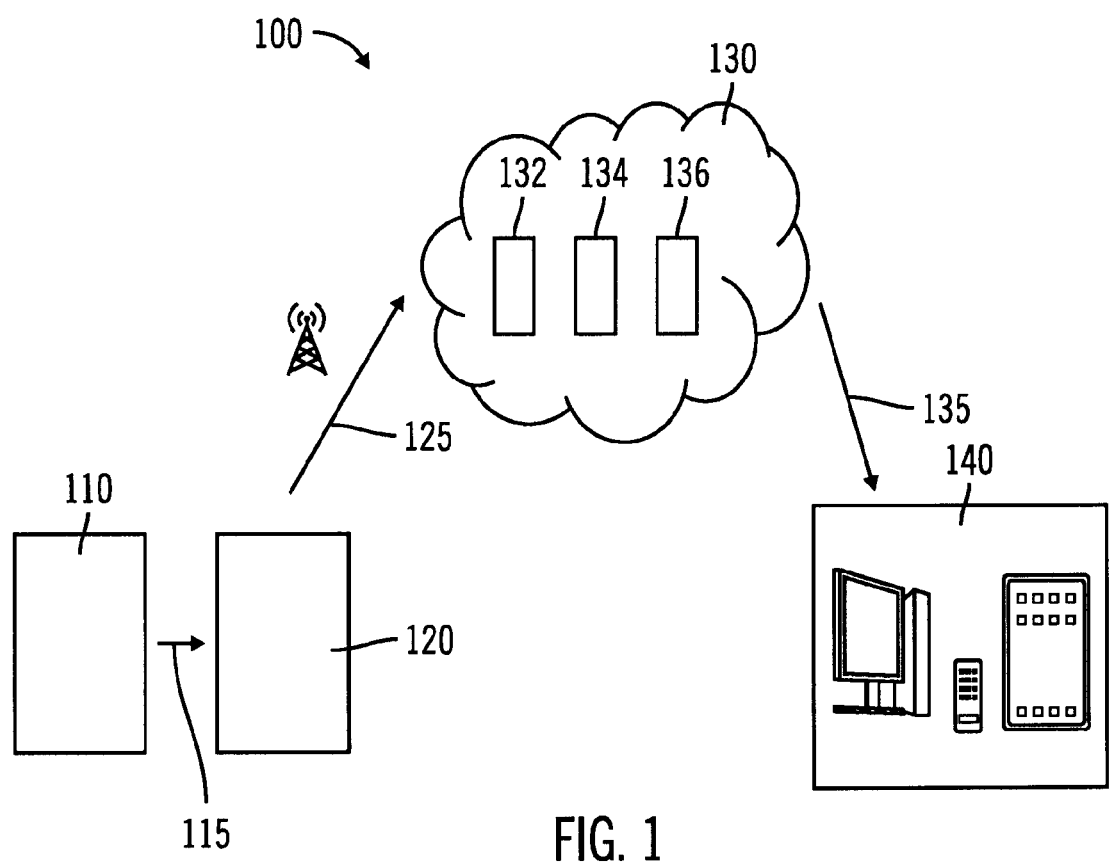
FIG. 1 is a block diagram of a variable data usage personal medical system made in accordance with the invention.

FIG. 1 is a block diagram of a variable data usage personal medical system made in accordance with the invention. The variable data usage personal medical system 100 is designed for use with a patient and includes a self-care device 110, a cellular communication device 120, and a cloud infrastructure 130. In this example, the variable data usage personal medical system 100 also includes an optional display device 140. The variable data usage personal medical system 100 allows the cloud infrastructure 130 to control the time interval at which the cellular communication device 120 communicates data from the self-care device 110 to the cloud infrastructure 130.

The self-care device 110 can be attached to the patient and is designed to be carried or worn by a patient. The self-care device 110 can be any personal medical device which delivers therapy to a patient and/or monitors a physiological parameter of the patient. Exemplary self-care devices include pumps, cell pumps, continuous glucose monitors, and the like. In one example, the self-care device 110 is an insulin delivery device. In another example, the self-care device 110 is a continuous glucose monitoring (CGM) device. In one embodiment, the self-care device 110 can both deliver therapy and monitor a physiological parameter. One example of such a device would be a paired insulin delivery and CGM device. Those skilled in the art will appreciate that the self-care device 110 can be any self-care device as desired for a particular application. The self-care device 110 generates self-care device data 115 and transmits the self-care device data 115 to the cellular communication device 120 at fixed intervals.

The cellular communication device 120 is operably connected to the self-care device 110. The cellular communication device 120 is a radio protocol converter and repeater device. The cellular communication device 120 stores the self-care device data 115 received by the cellular communication device 120 from the self-care device 110. The link between the cellular communication device 120 and the self-care device 110 can be wired or wireless, using standard protocols such as 802.11b/g/n. The radio protocol conversion can be stored in firmware in the cellular communication device 120. Exemplary cellular communication devices include CloudPost™ glucose monitors and remote controllers therefor, controllers, display meters, mobile phones, on-body communicators, on-body repeaters, and the like. In one embodiment, the cellular communication device 120 can request that the self-care device 110 send data stored in the self-care device 110 to provide the data backfill when the connection between the self-care device 110 and the cellular communication device 120 has been disconnected such that the cellular communication device 120 has not been receiving the self-care device data 115 from the self-care device 110. Thus, the cellular communication device 120 maintains a complete data record. In one embodiment, the cellular communication device 120 can be combined and integrated in a single package with the self-care device 110.

The cellular communication device 120 can register a count at an interval counter for each of the fixed intervals in which the transmitted self-care device data 115 is received. The interval counter can be incremented or decremented as desired for a particular application. When the interval counter equals a fixed interval index provided by the cloud infrastructure 130 and stored in the cellular communication device 120, the cellular communication device 120 can generate a data cellular packet 125, which includes the self-care device data stored in the cellular communication device 120 since data was last sent to the cloud infrastructure 130 plus overhead. The overhead can include information about the particular data cellular packet 125, such as identifiers, encryption keys, and the like. Those skilled in the art will appreciate that in the art will appreciate that the overhead can include any information desired for a particular application to facilitate communication between the cellular communication device 120 and the cloud infrastructure 130. The data cellular packet 125 is sent from the cellular communication device 120 to the cloud infrastructure 130 over a cellular network, i.e., a mobile radio network in which each land area is served by one or more local radio transceivers. In one embodiment, the cellular communication device 120 can store the data cellular packets when communication is lost between the cellular communication device 120 in the cloud infrastructure 130, and the cellular communication device 120 can send the stored data cellular packets when communication is restored.

The cloud infrastructure 130 receives the data cellular packet 125 from the cellular communication device 120, and can generate display data 135 from the data cellular packets received for transmission to the display device 140. The cloud infrastructure 130 can include a data center 132, a cloud application 134, and a database 136. Those skilled in the art will appreciate that the cloud infrastructure 130 can be a single device or can include multiple or distributed interconnected components performing the functions of the data center 132, the cloud application 134 and the database 136. The data cellular packet 125 can be received by the data center 132, processed by the cloud application 134, and stored in the database 136.

The cloud infrastructure 130 determines the value of the fixed interval index, which controls how often the cellular data packets are transmitted from the cellular communication device 120 to the cloud infrastructure 130. The cloud infrastructure 130 also transmits the value of the fixed interval index to the cellular communication device 124 storage in the cellular communication device 120. The cellular communication device 120 counts the number of times self-care device data 115 is received from the self-care device 110 by registering a count at an interval counter, then transmits the data cellular packet 125 when the interval counter equals the fixed interval index. The value of the fixed interval index can be selected as desired for a particular application. In one embodiment, the value of the fixed interval index can be a fixed integer. For example, the fixed integer can be selected based on factors such as medical condition and history of a particular patient, statistical analysis of patient group experience, or the like. In another embodiment, the value of the fixed interval index can be selected by the cloud infrastructure 130 based on activity in the variable data usage personal medical system 100, such as viewing data on the display device 140. In another embodiment, the value of the fixed interval index can be selected based on communication costs, so that the data cellular packets are transmitted from the cellular communication device 122 the cloud infrastructure 130 more often when communication costs are low. Exemplary cloud infrastructures include CareLink® Personal Software, SMS aggregators, servers, computers, and the like.

The display device 140 can be any human machine interface in communication with the cloud infrastructure 130 capable of receiving and displaying the display data 135. Exemplary displays for display devices 140 include displays on dedicated display devices, consumer devices, mobile phones, computers (e.g., desktops, laptops), computer tablets, Internet-enabled televisions, and the like. In one embodiment, the display device 140 can be integrated with the self-care device 110 and/or the cellular communication device 120.

The display device 140 can be updated continuously or periodically. The display device 140 can generate a display device data request when the display device 140 is enabled, i.e., when the display device is energized and/or being used. The display device data request is transmitted from the display device 140 to the cloud infrastructure 130. In one continuous update embodiment and in response to the display device data request, the cloud infrastructure 130 sends a wake up message to the cellular communication device 120, followed by repeated cloud infrastructure data requests to the cellular communication device 120. In response to the repeated cloud infrastructure data requests, the cellular communication device 120 sends a data cellular packet 125 to the cloud infrastructure 130 every time the self-care device 110 sends the self-care device data 115 to the cellular communication device 120, i.e., each time the interval counter equals the fixed interval index. The cloud infrastructure 130 then generates continuous display data from the data cellular packets and provides the display data 135 to the display device 140, providing a continuous update of the display device 140.

In another continuous update embodiment, the cellular communication device 120 can include a continuous communication index that is responsive to a toggle command from the cloud infrastructure 130. The display device 140 can generate a display device data request when the display device is enabled and transmit the display device data request to the cloud infrastructure 130. In response, the cloud infrastructure 130 can send a toggle command to the cellular communication device 120 to toggle the value of a continuous communication index. This, in turn, toggles the operating mode of the cellular communication device 120 from the current mode to the alternate mode, i.e., from continuous to normal or from normal to continuous. In the normal mode, the fixed interval index governs how often the cellular communication device 120 sends the data cellular packet 125 to the cloud infrastructure 130. In the continuous mode, the cellular communication device 120 sends the data cellular packet 125 to the cloud infrastructure 130 every time the cellular communication device 120 receives self-care device data 115 from the self-care device 110. The cloud infrastructure 130 can send another toggle command to the cellular communication device 120 that changes the value of the continuous communication index back to its initial value, for example, returning the cellular communication device 120 to the normal mode when the display device 140 is turned off.

In yet another continuous update embodiment, the fixed interval index can be changed to provide a continuous update. The display device 140 can generate a data interval increase request when the display device 140 is enabled. The data interval increase request is transmitted from the display device 140 to the cloud infrastructure 130, which sends a wake up message and new value for the fixed interval index to the cellular communication device 120. The new value is typically less than the present value of the fixed interval index, so that the data cellular packets 125 are sent to the cloud infrastructure 130 more often to keep the display device 140 current. In one example, the new value is one, so that a data cellular packet 125 is transmitted to the cloud infrastructure 130 every time the cellular communication device 120 receives self-care device data 115 from the self-care device 110.

In a periodic update embodiment, the display device 140 can generate a display device data request when the display device is enabled and transmit the display device data request to the cloud infrastructure 130. In response to the display device data request, the cloud infrastructure 130 sends the display data 135 generated from the most recent data cellular packet 125 received at the cloud infrastructure 130 to the display device 140. In response to the display device data request, the cloud infrastructure 130 also sends a single cloud infrastructure data request to the cellular communication device 120. In response to the single cloud infrastructure data request, the cellular communication device 120 sends a data cellular packet 125 containing the latest self-care device data 115 stored in the cellular communication device 120 to the cloud infrastructure 130, which generates latest display data 135 from the data cellular packet 125 and sends the latest display data 135 to the display device 140. Thus, the display device 140 displays the most recent data received by the cloud infrastructure 130 with updated data requested from the cellular communication device 120.

The improvement in data usage with the variable data usage personal medical system can be illustrated by looking at data usage at different fixed interval indices. As described above, the data packet includes overhead providing information about the transmission and a payload including stored self-care device data. When the overhead requires 565 bits and the payload taken every 5 minutes is 107 bits, the data usage is 5.8 Mb per month when the fixed interval index causes the five minute data packet of 672 bits [565+107] to be sent every 5 minutes. Using the same 565 bits for overhead plus 107 bits of payload taken every 5 minutes, the data usage is 1.7 Mb per month when the fixed interval index causes the thirty minute data packet of 1207 bits [565+(6*107)] to be sent every 30 minutes.

Figure 2:
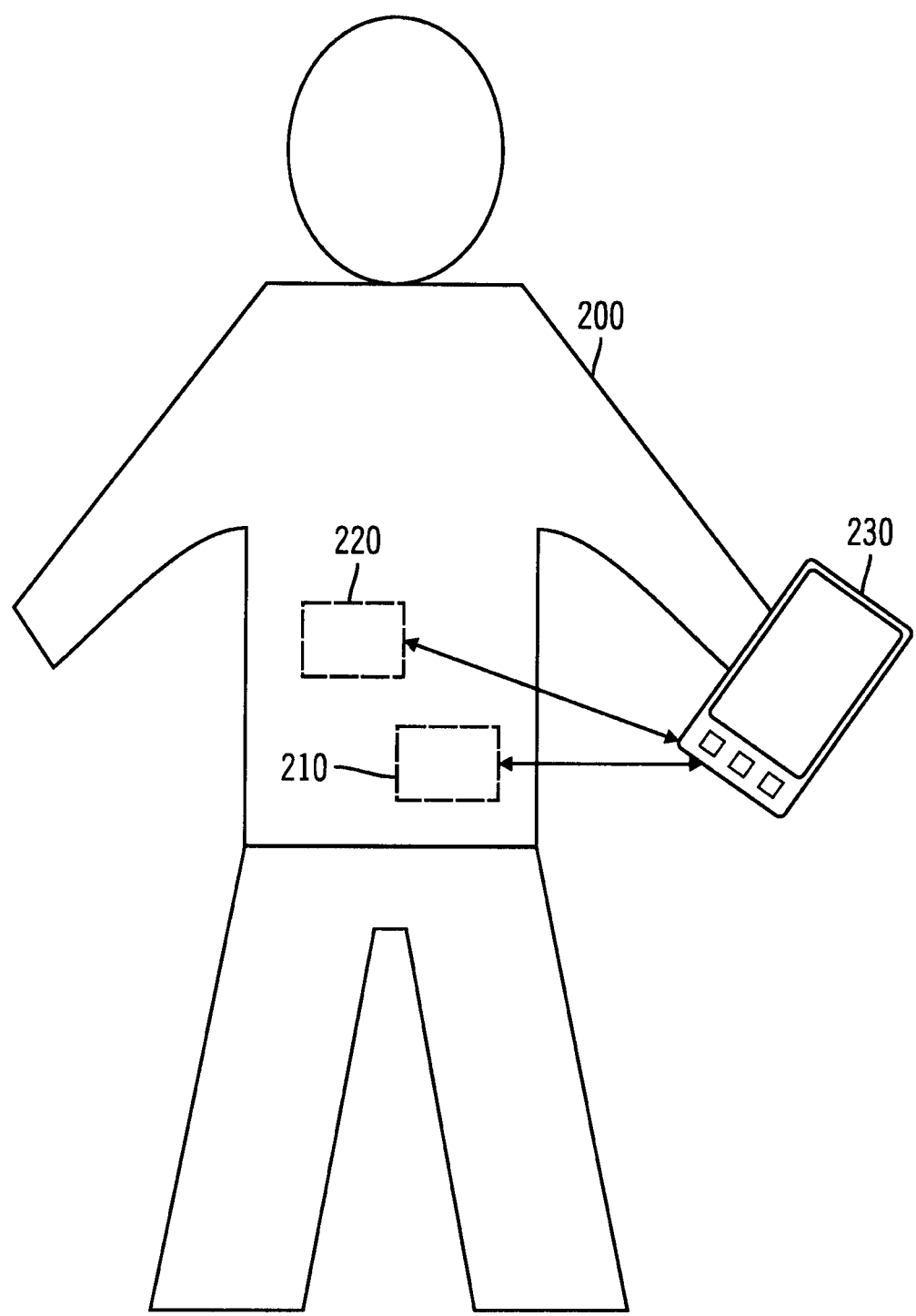
FIG. 2 is a schematic diagram of self-care devices and a cellular communication device for a variable data usage personal medical system made in accordance with the invention.

FIG. 2 is a schematic diagram of self-care devices and a cellular communication device for a variable data usage personal medical system made in accordance with the invention. In this example, the patient 200 and is wearing two self-care devices, a therapy administration device 210 and a physiological monitoring device 220, both of which are in wired and/or wireless communication with a cellular communication device 230. In one embodiment, the therapy administration device 210 is an insulin delivery device and the physiological monitoring device 220 is a continuous glucose monitoring (CGM) device. The self-care device as defined herein can be any personal medical device designed to be carried or worn by a patient.

Figure 3:
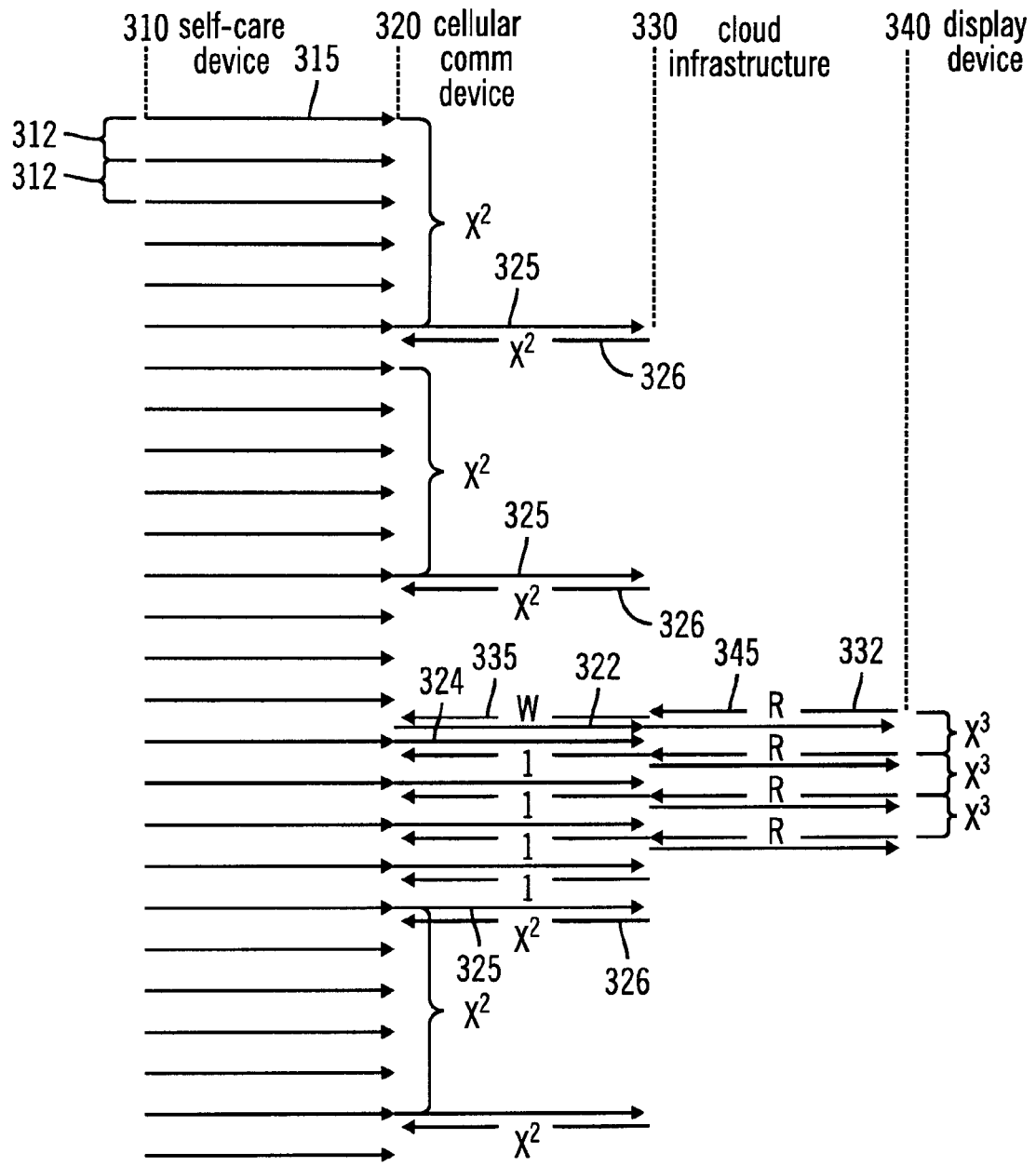
FIG. 3 is a timing chart of communications for a variable data usage personal medical system made in accordance with the invention.

FIG. 3 is a timing chart of communications for a variable data usage personal medical system made in accordance with the invention. The communications occur between the components described above: a self-care device 310, a cellular communication device 320, a cloud infrastructure 330, and a display device 340.

At 315, the self-care device 310 sends self-care device data to the cellular communication device 320 at a fixed interval 312, such as 5 minutes in this example. The cellular communication device 320 receives and stores the self-care device data, and increments and interval counter each time the self-care device data is received.

At 325, the cellular communication device 320 sends a data cellular packet to the cloud infrastructure 330 when the interval counter equals a fixed interval index. The data cellular packet is generated by the cellular communication device and includes overhead plus stored self-care device data. In this example, the fixed interval index is 6 so that the data cellular packet is transmitted to the cloud infrastructure 330 every 30 minutes. At 326, the cloud infrastructure 330 can return an optional data received response to the cellular communication device 320. The cycle of data transfer from the self-care device 310 to the cellular communication device 320, followed by the less frequent transfer of data from the cellular communication device 320 to the cloud infrastructure 330 can be repeated indefinitely.

When the display device 340 is enabled, the display device 340 sends a display device data request to the cloud infrastructure 330 at 345. The cloud infrastructure 330 sends a wake up message to the cellular communication device 320 in response at 335. The cellular communication device 320 sends the latest data cellular packet to the cloud infrastructure 330 in response to the wake up message at 322. The cloud infrastructure 330 generates display data including the latest data cellular packet and transmits the display data to the display device 340 at 332. At 324, the cellular communication device 320 transmits a data cellular packet to the cloud infrastructure 330 when the interval counter equals the fixed interval index.

After a fixed interval, the display device 340 sends another display device request to the cloud infrastructure 330 and the cycle is repeated with the return of the latest display data to the display device 340. When the display device 340 is disabled, display data is no longer transmitted from the cloud infrastructure 330 to the display device 340, and the variable data usage personal medical system returns to the cycle of data transfer from the self-care device 310 to the cellular communication device 320, followed by the less frequent transfer of data from the cellular communication device 320 to the cloud infrastructure 330.

Those skilled in the art will appreciate that the communications for the variable data usage personal medical system can include security features as desired for a particular application. In one example, devices which desire to communicate, such as the cellular communication device and the cloud infrastructure, can employ a handshake protocol to verify each other's identity before data is sent between them. In another example, devices can establish a virtual private network across publicly accessible communications networks. In yet another example, the data being transmitted can be encrypted to verify integrity and security.

Figure 4:
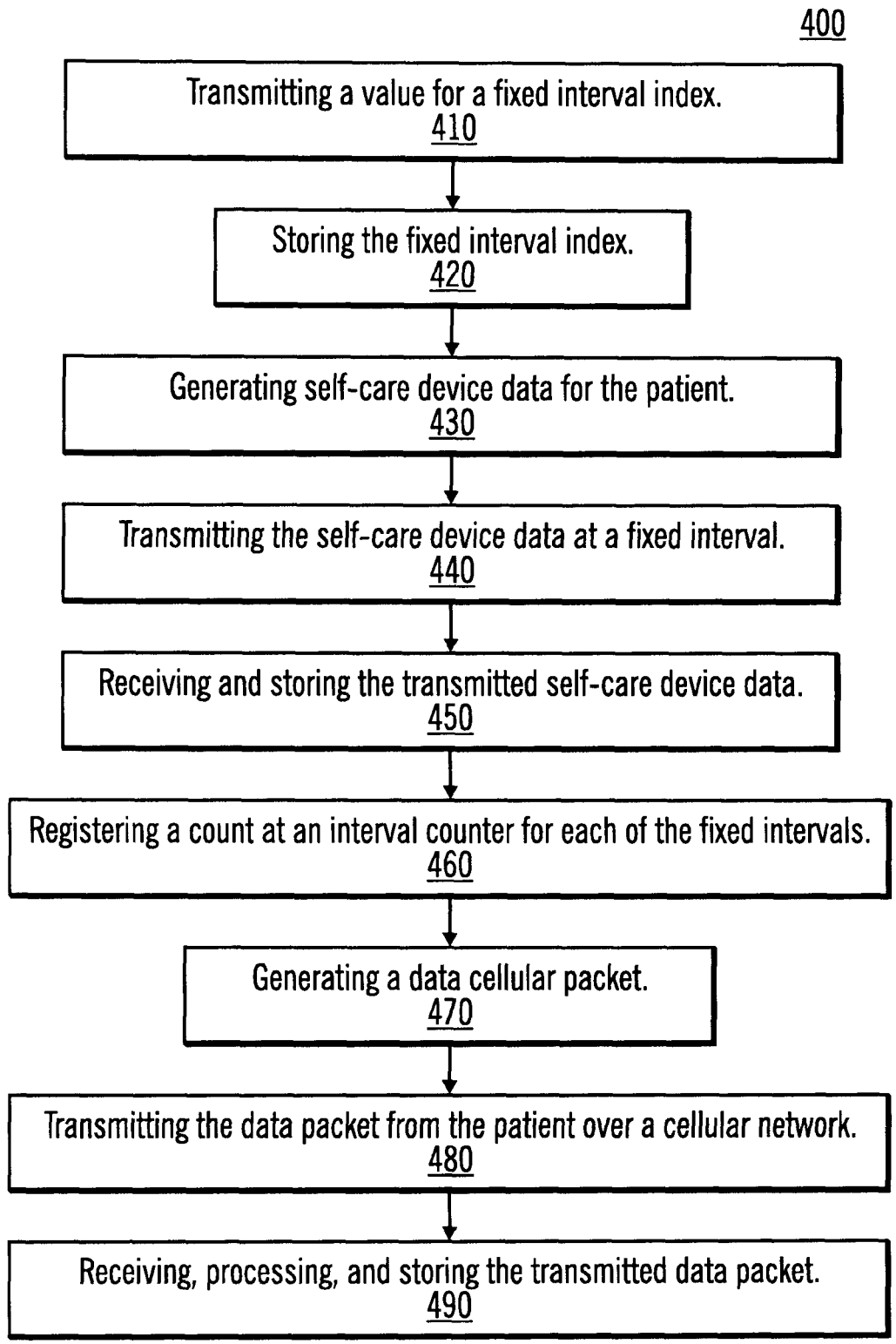
FIG. 4 is a flow chart of a method of personal medical variable data usage for a patient in accordance with the invention.
Figure 5H:
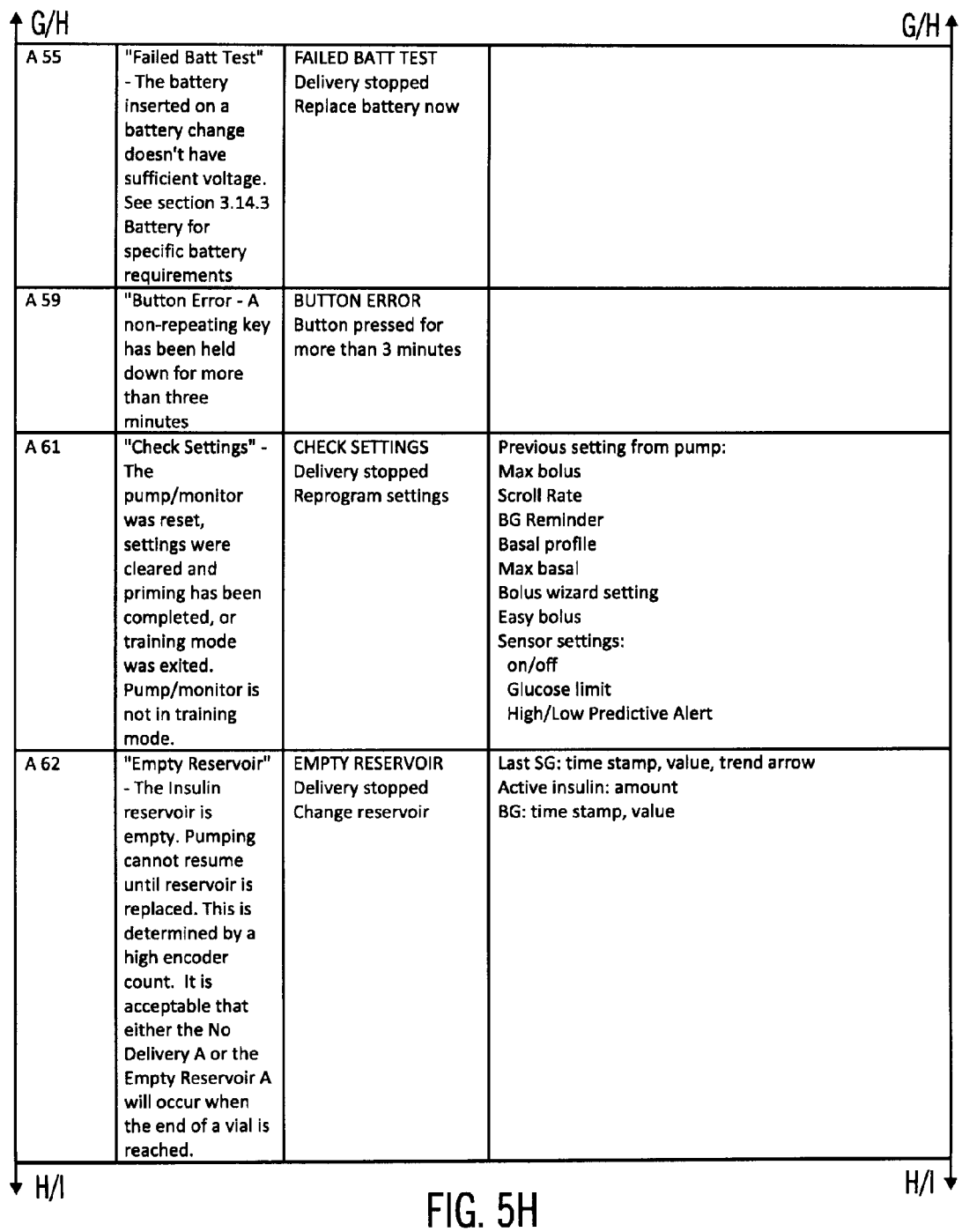

FIG. 4 is a flow chart of a method of personal medical variable data usage for a patient in accordance with the invention. The method 400 includes transmitting a value for a fixed interval index 410 remote from the patient; storing the fixed interval index 420 at the patient; generating self-care device data for the patient 430; transmitting the self-care device data at a fixed interval 440; receiving and storing the transmitted self-care device data 450; registering a count at an interval counter for each of the fixed intervals 460 in which the transmitted self-care device data is received; generating a data cellular packet 470 from overhead plus the stored self-care device data when the interval counter equals the fixed interval index; transmitting the data packet from the patient over a cellular network 480; and receiving, processing, and storing the transmitted data packet 490 remote from the patient. The term "at the patient" as defined herein means that the action occurs on, in, or near the patient; the term "remote from the patient" as defined herein means that the action occurs away from the body of the patient at a distance. For example, storing a fixed interval index at the patient can be performed by storing the fixed interval index in a cellular communication device, while receiving, processing, and storing the transmitted data packet remote from the patient can be performed in the cloud infrastructure. In one embodiment, the method 400 can further include generating display data from the transmitted data packet, and presenting the display data. In another embodiment, the method 400 can further include transmitting an alarm packet with accompanying data from the patient, and optionally adjusting therapy for the patient based on the accompanying data. The method 400 can be carried out on a variable data usage personal medical system as described for FIG. 1.

FIG. 5A-5I is a table of alarms and accompanying data for a variable data usage personal medical system made in accordance with the invention. The table includes the alarm number 510, the alarm name 520 with definition, the notification text message 530, and the accompanying data 540. When the self-care device detects an unusual condition and sends an alarm packet to the cloud infrastructure through the cellular communication device, the alarm packet includes the alarm number as an identifier plus the accompanying data for use in making therapy adjustments. Accompanying data as defined herein is any data available at the cellular communication device which is useful to the cloud infrastructure in making therapy adjustments. For example, referring to alarm number A101 of FIG. 5A, the alarm is transmitted from the self-care device when the self-care device measures glucose above a user specified high limit. The accompanying data to be sent in the alarm packet includes data useful in making therapy adjustments, such as information concerning time, injection history, glucose measurement history, patient activity history, and the like. Those skilled in the art will appreciate that alarms and accompanying data other than the examples of FIG. 5A-5I can be used as desired for a particular application. For example, the accompanying data can be used for therapy management by patients, health care providers, health service payors, caregivers, and the like.

It is important to note that FIGS. 1-5I illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A variable data usage personal medical system for use with a patient comprising:
   a self-care device attached to the patient, the self-care device being operable to generate self-care device data and to transmit the self-care device data at a fixed interval;
   a cellular communication device operably connected to the self-care device, the cellular communication device being operable to receive and store the transmitted self-care device data, to store an interval counter and to increment the interval counter for each of the fixed intervals in which the transmitted self-care device data is received, and in response to determining that the interval counter equals a fixed interval index, to generate a data cellular packet from overhead plus the stored self-care device data and to transmit the data packet, wherein the fixed interval index controls how often data packets are transmitted from the cellular communication device; and
   a cloud infrastructure operably connected to the cellular communication device over a cellular network, the cloud infrastructure being operable to receive, process, and store the transmitted data packet;
   wherein the cellular communication device is operable to store the fixed interval index and the cloud infrastructure is operable to transmit a value for the fixed interval index to the cellular communication device for storage.

2. The system of claim 1 wherein the cloud infrastructure is further operable to generate and transmit display data from the transmitted data packet, and the system further comprises a display device operably connected to the cloud infrastructure, the display device being operable to present the transmitted display data.

3. The system of claim 2 wherein:
the display device is further operable to generate a first display device data request when the display device is enabled and transmit the first display device data request to the cloud infrastructure;
the cloud infrastructure is further operable to send a wake up message to the cellular communication device in response to the first display device data request;
the display device is further operable to generate repeated display device data requests and transmit the repeated device data requests to the cloud infrastructure;
the cloud infrastructure is further operable to send repeated cloud infrastructure data requests to the cellular communication device;
the cellular communication device is further operable to send data cellular packets to the cloud infrastructure in response to each of the repeated cloud infrastructure data requests, one of the data cellular packets being sent each time the self-care device sends self-care device data to the cellular communication device;
the cloud infrastructure is further operable to generate continuous display data from the data cellular packets and transmit the continuous display data to the display device; and
the display device is further operable to display the continuous display data.

4. The system of claim 2 wherein:
the display device is further operable to generate a first display device data request when the display device is enabled and transmit the first display device data request to the cloud infrastructure;
the cloud infrastructure is further operable to send a toggle command to the cellular communication device in response to the first display device data request to toggle a value of a continuous communication index of the cellular communication device;
the cellular communication device is further operable to change operating state in response to the value of the continuous communication index, the operating state being one of a continuous mode and a normal mode;
wherein, in the continuous mode, the cellular communication device sends the data cellular packet to the cloud infrastructure every time the cellular communication device receives self-care device data from the self-care device; and
in the normal mode, the fixed interval index governs how often the cellular communication device sends the data cellular packet to the cloud infrastructure.

5. The system of claim 2 wherein the value for the fixed interval index is a first value, the display device is further operable to generate a data interval increase request when the display device is enabled, the data center is further operable to send a wake up message and a second value for the fixed interval index to the cellular communication device in response to the data interval increase request, the first value being greater than the second value.

6. The system of claim 5 wherein the second value is 1, the cellular communication device being operable to transmit the data packet to the data center at each of the fixed intervals.

7. The system of claim 2 wherein:
the display device is further operable to generate a first display device data request when the display device is enabled and transmit the first display device data request to the cloud infrastructure;
the cloud infrastructure is further operable to send the displayed data generated from the most recent data cellular packet received the cloud infrastructure to the display device in response to the first display device data request;
the cloud infrastructure is further operable to send a single cloud infrastructure data request to the cellular communication device in response to the first display device data request;
the cellular communication device is further operable to send the data cellular packet including latest self-care device data stored in the cellular communication device to the cloud infrastructure in response to the single cloud infrastructure data request; and
the cloud infrastructure is further operable to generate latest display data from the data cellular packet including latest self-care device data and to transmit the latest display data to the display device.

8. The system of claim 2 wherein the display device is selected from the group consisting of dedicated display devices, consumer devices, mobile phones, desktop computers, laptop computers, computer tablets, and Internet-enabled televisions.

9. The system of claim 2 wherein the display device is integrated with at least one of the self-care device and the cellular communication device.

10. The system of claim 1 wherein the self-care device is selected from the group consisting of a personal medical device delivering therapy to the patient, a personal medical device monitoring a physiological parameter of the patient, and a combination thereof.

11. The system of claim 1 wherein the self-care device is selected from the group consisting of an insulin delivery device and a continuous glucose monitoring device.

12. The system of claim 1 wherein the self-care device and the cellular communication device are combined and integrated in a single package.

13. The system of claim 1 wherein the self-care device is further operable to transmit an alarm packet with accompanying data.

14. The system of claim 1 wherein the cloud infrastructure comprises a data center operable to receive the data cellular packet, a cloud application operable to process the received data cellular packet, and a database operable to store the processed data cellular packet.

15. A method of personal medical variable data usage for a patient comprising:
transmitting a value for a fixed interval index remote from the patient;
storing the fixed interval index at the patient;
generating self-care device data for the patient;
transmitting the self-care device data at a fixed interval;
receiving and storing the transmitted self-care device data;
storing an interval counter and incrementing the interval counter for each of the fixed intervals in which the transmitted self-care device data is received;
generating a data cellular packet from overhead plus the stored self-care device data in response to determining that the interval counter equals the fixed interval index;
transmitting the data packet from the patient over a cellular network, wherein the fixed interval index controls how often data packets are transmitted; and
receiving, processing, and storing the transmitted data packet remote from the patient.

16. The method of claim 15 further comprising generating display data from the transmitted data packet, and presenting the display data.

17. The method of claim 15 further comprising transmitting an alarm packet with accompanying data from the patient.

18. The method of claim 17 further comprising adjusting therapy for the patient based on the accompanying data.

* * * * *